(12) United States Patent
Gilbert (10) Patent No.: US 8,814,864 B2
(45) Date of Patent: Aug. 26, 2014

(54) METHOD OF MANUFACTURING TISSUE SEALING ELECTRODES

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 835 days.

(21) Appl. No.: 12/861,198

(22) Filed: Aug. 23, 2010

(65) Prior Publication Data

US 2012/0046662 A1  Feb. 23, 2012

(51) Int. Cl.
*A61B 18/14* (2006.01)

(52) U.S. Cl.
USPC .............................................. 606/51; 606/52

(58) Field of Classification Search
USPC ...................................................... 606/45–52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,611,798 A | 3/1997 | Eggers |
| 5,626,578 A | 5/1997 | Tihon |
| D384,413 S | 9/1997 | Zlock et al. |
| 5,755,717 A | 5/1998 | Yates et al. |
| 5,779,701 A | 7/1998 | McBrayer et al. |
| H1745 H * | 8/1998 | Paraschac ....................... 606/51 |
| D402,028 S | 12/1998 | Grimm et al. |
| 5,849,022 A | 12/1998 | Sakashita et al. |
| 5,891,142 A | 4/1999 | Eggers et al. |
| 5,911,719 A | 6/1999 | Eggers |
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

(Continued)

*Primary Examiner* — Michael Peffley (57) ABSTRACT

The present disclosure relates to an electrode assembly for use with an electrosurgical instrument. The electrode assembly includes a pair of opposing jaw members and an electrode positioned on each jaw member. One or both of the electrodes includes a tissue contacting surface that has an outer periphery and defines a side surface depending therefrom. The tissue contacting surface and the side surface include a conjoining edge formed at a first predetermined angle that defines a first linear transition zone dimensioned to reduce arcing between the opposing jaw members during activation of the electrosurgical instrument.

14 Claims, 4 Drawing Sheets

(56) References Cited

U.S. PATENT DOCUMENTS

| | | |
|---|---|---|
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| 6,736,813 B2 * | 5/2004 | Yamauchi et al. ............... 606/48 |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,932,810 B2 | 8/2005 | Ryan |
| D509,297 S | 9/2005 | Wells |
| 6,953,461 B2 | 10/2005 | McClurken et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,160,298 B2 * | 1/2007 | Lawes et al. ..................... 606/51 |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee et al. |
| 7,329,257 B2 * | 2/2008 | Kanehira et al. ................ 606/52 |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 8,070,748 B2 | 12/2011 | Hixson et al. |
| 8,092,451 B2 | 1/2012 | Schechter et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,215,182 B2 | 7/2012 | Artale et al. |
| 8,257,352 B2 | 9/2012 | Lawes et al. |
| 8,266,783 B2 | 9/2012 | Brandt et al. |
| 8,267,935 B2 * | 9/2012 | Couture et al. .................. 606/51 |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 8,348,948 B2 | 1/2013 | Bahney |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,556,929 B2 | 10/2013 | Harper et al. |
| 8,568,397 B2 | 10/2013 | Horner et al. |
| 8,568,412 B2 | 10/2013 | Brandt et al. |
| 2006/0116675 A1 | 6/2006 | McClurken et al. |
| 2007/0173804 A1 | 7/2007 | Wham et al. |
| 2007/0173811 A1 | 7/2007 | Couture et al. |
| 2009/0157071 A1 | 6/2009 | Wham et al. |
| 2009/0157072 A1 | 6/2009 | Wham |
| 2009/0157075 A1 | 6/2009 | Wham et al. |
| 2010/0280511 A1 | 11/2010 | Rachlin et al. |
| 2010/0331839 A1 | 12/2010 | Schechter et al. |
| 2011/0004210 A1 | 1/2011 | Johnson et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060335 A1 | 3/2011 | Harper et al. |
| 2011/0071523 A1 | 3/2011 | Dickhans |
| 2011/0073594 A1 | 3/2011 | Bonn |
| 2011/0077648 A1 | 3/2011 | Lee et al. |
| 2011/0118736 A1 | 5/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301604 A1 | 12/2011 | Horner et al. |
| 2011/0319886 A1 | 12/2011 | Chojin et al. |
| 2011/0319888 A1 | 12/2011 | Mueller et al. |
| 2012/0022532 A1 | 1/2012 | Garrison |
| 2012/0029515 A1 | 2/2012 | Couture |
| 2012/0041438 A1 | 2/2012 | Nau, Jr. et al. |
| 2012/0046659 A1 | 2/2012 | Mueller |
| 2012/0046660 A1 | 2/2012 | Nau, Jr. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009 317 | 10/2007 |
| DE | 19738457 | 1/2009 |
| EP | 1159926 | 12/2001 |
| EP | 1177771 | 2/2002 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |

(56) References Cited

FOREIGN PATENT DOCUMENTS

| | | |
|---|---|---|
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'L Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

(56) References Cited

OTHER PUBLICATIONS

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 09/387,883, filed Sep. 1, 1999, Schmaltz.
U.S. Appl. No. 09/591,328, filed Jun. 9, 2000, Ryan.
U.S. Appl. No. 12/336,970, filed Dec. 17, 2008, Sremcich.

* cited by examiner

METHOD OF MANUFACTURING TISSUE SEALING ELECTRODES

BACKGROUND

1. Technical Field

The present disclosure relates to electrosurgical instruments used for open and endoscopic surgical procedures. More particularly, the present disclosure relates to a method of manufacturing tissue sealing electrodes for sealing vessels and vascular tissue.

2. Description of Related Art

Monopolar and bipolar instruments are among the most commonly utilized instruments in the field of electrosurgery. Briefly, monopolar instruments utilize one or more active electrode(s) that are associated with a clamping electrode (e.g., jaw members) and a remote patient return electrode or pad that is attached externally to the patient. Bipolar electrosurgical forceps utilize two generally opposing electrodes. Both electrodes are generally disposed on an inner facing or opposing surfaces of the jaw members which are, in turn, electrically coupled to an electrosurgical generator.

Essentially, during monopolar surgical treatment, energy travels from the active electrode(s) to the surgical site, through the patient and to the return electrode or pad. In the situation where more than one electrode is utilized, all of the active electrodes are charged to the same electric potential. On the other hand, during bipolar surgical treatment, each opposing electrode is charged to a different electric potential. Since tissue is a conductor of electrical energy, when the electrodes are utilized to clamp or grasp tissue therebetween, the electrical energy can be selectively transferred from one electrode to the other electrode, through the tissue, to effectively seal the tissue.

The construction and mechanics of surgical electrodes both play a major role in affecting a proper seal with tissue and vessels, especially larger vessels. For example, the seal quality may be affected by the pressure applied to the vessels and/or the sealing area of the electrodes. Accordingly, the rate and effectiveness at which tissue and/or vessels are sealed depends on the jaw pressure and the sealing area (e.g., surface area of electrode) of the jaw members. With this concept in mind, a larger jaw requires more energy to compensate for the greater surface area, alongside with the greater amount of tissue being clamped or grasped by the larger jaw members. However, in larger jaw members, when the pressure is sufficiently increased, less electrosurgical energy is required. This is evidenced by the bioheat equation and the Arrhenius function, which confirms that temperature is related to surface area and tissue heating becomes a function of temperature with respect to time, as shown below in the bioheat equation (1):

$$T = \frac{1}{\sigma \rho c} * J^2 t + T_0 \quad (1)$$

where "T" is temperature, "σ" is Stefan-Boltzmann constant, "ρ" is density of tissue, "c" is the specific heat of tissue, "J" is the current density and "t" is time. It is important to note that current density depends on the area through which current is conducted. For example, a small area can amplify the effect of current on temperature.

As discussed above, tissue heat is calculated using the Arrhenius function (2) shown below:

$$\Omega = \int A e^{\left(\frac{-Ea}{R} * \frac{1}{T}\right)} dt \quad (2)$$

where "Ω" is a dimensionless burn parameter (e.g., Ω=1 means first degree burn), "A" is a frequency factor, "E" is the activation energy, "R" is the universal gas constant, and "T" is tissue temperature.

With reference to the equations (1) and (2), the sealing quality of tissue (with respect to current density delivered over time) and the temperature of tissue that is reached for a quality seal (or even coagulation), both depend on the characteristics of the tissue clamped, held and/or grasped between the jaw members (e.g., 1/σρc). However, it should be noted that calculations of equations (1) and (2) will assume that the pressure exerted on the tissue is evenly distributed and that during the clamping process the tissue flow is laminar. That is, the tissue does not form any or have any bubbles and/or gaps, while the tissue is grasped between the jaw members.

Taking the above-described phenomena into consideration, the pressure applied by the electrodes, via the jaw members, plays an important role towards the changing tissue impedance during a tissue sealing procedure that ultimately results in a successful tissue seal. Some tissue factors that correlate with the amount of pressure applied are, for example, but not limited to: the amount of volume of tissue; the density of tissue; the viscosity of the tissue; and the specific heat of the tissue. More specifically, the amount or volume of tissue grasped by the jaw members (e.g., the electrodes) determines the amount of tissue contact the electrodes require and the distance between the electrodes. With regard to tissue density, the density of tissue grasped relates to pressure because if the jaws exert a very high pressure, the stress limit of the tissue may be exceeded, thus bursting and/or rupturing a majority of cells of the tissue. Knowing or measuring the overall viscosity of the tissue is important during clamping of the jaws because discontinuities may cause turbulent flow that would cause unwanted bubbles or gaps. Specific heat of the tissue relates to: the pressure applied during the application of pressure on tissue; the changes in cell shape; and/or rupturing may affect the specific heat in some way.

Another issue that may arise during electrosurgical surgery is "arcing" between electrodes. Arcing, which is also commonly referred to as electrical arcing, is an electrical breakdown of a gas which produces an ongoing plasma discharge that results from a current flowing through nonconductive media, for example, air. Some factors that affect arcing are the so-called "clearance distance" and the so-called "creepage distance" between the electrodes. The clearance distance is the shortest distance between two conductive media measured through air. During surgery, air clearance is of concern as high transient voltages can arc over or breach a dielectric barrier. The creepage distance is the shortest path between two conductive media measured along the surface of nonconductive media. Given a high enough potential applied between two points on nonconductive media, the right environmental conditions, and sufficient time, the surface of the nonconductive media may break down resulting in an arc between conductive surfaces. This is called "tracking." Tracking occurs only with surfaces and is not typically associated across air.

SUMMARY

The present disclosure relates to an electrode assembly for use with an electrosurgical instrument. The electrode assembly includes a pair of opposing jaw members and an electrode positioned on each jaw member. One or both of the electrodes includes a tissue contacting surface that has an outer periphery and defines a side surface depending therefrom. The tissue contacting surface and the side surface include a conjoining edge formed at a first predetermined angle that defines a first linear transition zone dimensioned to simultaneously reduce arcing between the opposing jaw members during activation of the electrosurgical instrument and maintain laminar flow of the tissue during clamping.

In one embodiment, the conjoining edge of one or both of the electrodes is formed by the first predetermined angle to define the first linear transition zone and a second predetermined angle to define a second linear transition zone.

In embodiments, the conjoining edge may be calculated from a hyperbolic equation, a parabolic equation, exponential equation, a clothoid equation, Bernoulli's equation, or an Archimedean equation.

In embodiments, the conjoining edge of one or both of the electrodes may include a chamfered configuration that defines an angle relative to the tissue contacting surface. The angle may be about 5 degrees to about 10 degrees.

The present disclosure also relates to a method for manufacturing an electrode assembly for use with an electrosurgical instrument. The method includes providing an electrode assembly having a pair of opposing jaw members and an electrode positioned on each jaw member. One or both of the electrodes includes a tissue contacting surface that has an outer periphery that defines a side surface depending therefrom. In another step, a conjoining edge if formed at a first predetermined angle relative to and disposed between the tissue contacting surface and the side surface. The conjoining edge defines a linear transition zone dimensioned to simultaneously reduce arcing between opposing jaw members during activation of the electrosurgical instrument and maintain laminar flow of the tissue during clamping.

In embodiments, the forming of the conjoining edge may be calculated from a hyperbolic equation, a parabolic equation, exponential equation, a clothoid equation, Bernoulli's equation, or an Archimedean equation.

In embodiments, the forming of the conjoining edge may include the formation of a second predetermined angle that defines a second linear transition zone. The first and second linear transition zones may also be calculated from the equations consisting of a hyperbolic equation, a parabolic equation, exponential equation, a clothoid equation, Bernoulli's equation, or an Archimedean equation.

In embodiments, another method for manufacturing an electrode assembly includes providing an electrode on a jaw member that includes a side surface having a vertical configuration relative to the jaw member and a tissue contacting sealing surface having a horizontal configuration relative to the jaw member. In another step, the edges of the electrode are chamfered at a predetermined angle relative to the side edges and the inner facing sealing surfaces. The chamfered edges are configured to reduce a width of the inner facing sealing surfaces and create a linear transition zone to reduce arcing between opposing jaw members. The step of chamfering may include cutting or molding. In embodiments, the predetermined angle may be about 5 degrees to about 10 degrees.

BRIEF DESCRIPTION OF THE DRAWINGS

Various embodiment of the subject instrument are described herein with reference to the drawings wherein.

DETAILED DESCRIPTION

Embodiments of the presently-disclosed electrosurgical instrument are described in detail with reference to the drawings wherein like reference numerals identify similar or identical elements. As used herein, the term "distal" refers to that portion which is further from a user while the term "proximal" refers to that portion which is closer to a user. As used herein, the term "easement" refers to a portion of an electrode that is between a tissue contacting surface and a side surface of the electrode, which will be described in greater detail below.

In accordance with embodiments of the present disclosure, an electrode assembly may be manufactured wherein each electrode includes a so-called easement or linear transition zone to facilitate a uniform current density distribution to a portion of the electrode assembly and ensure laminar tissue flow when the electrode assembly is grasping tissue. In this manner, during tissue treatment (e.g., coagulation or sealing) of body tissue, unintended side effects to treated tissue and surrounding untreated tissue is substantially reduced. The easement of each electrode may be configured at an angle that may be derived empirically and/or by various embodiments of novel methods that will be described herein. In one embodiment, a method of manufacturing the easement is calculated by finite element analysis using homogeneous tissue models or other suitable tissue models that include both electrical and mechanical properties. In another embodiment, a method of manufacturing the easement is calculated by estimating an angle between the horizontal and side surfaces based on an approximation for a homogeneous tissue model (e.g., may be about 5 degrees to about 10 degrees, assuming the efficacy is dependent on a tangent function of the jaw members).

The present disclosure also provides electrodes that are configured to avoid so-called "hot spots" of high current density and/or contact points that may allow an arc to form on or between the electrodes. Essentially, an easement may be provided between the tissue contacting surface and the side surface of the electrode to substantially reduce these "hot spots" or discontinuities.

Figure 2A:
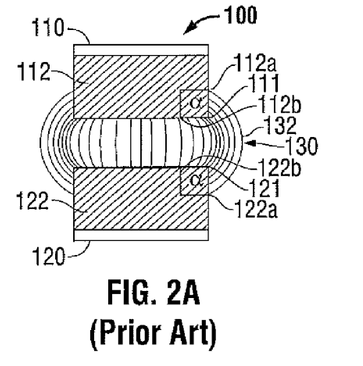
FIG. 2A is a front, cross-sectional view of a prior art electrode assembly showing a schematically-illustrated electric field plot.

One advantage in providing easements on electrodes, in particular when provided on larger electrodes, is that easements provide a gradual change (e.g., a smooth transition) along the dimension of the electrode. For example, the tissue contacting surface may transition to the side surface via an easement (e.g., a calculated curve) rather than a straight edge (e.g., corner), as shown in FIG. 2A. In this manner, the change in the electric field density (as shown in FIG. 4A) between the electrode edges travels through a linear transition zone (e.g., easement), rather than abrupt changes in electric field density associated with squared edges (as shown in FIG. 2A). FIGS. 2A-4B illustrate a schematic of electric field contour lines 132, 232 and 332, stress tensors 136 and 236 of tensor field plots 135, 235 and 335 and laminar tissue flow tensors 138, 238 and 338 during clamping or grasping of tissue for each of the configurations discussed below.

Figure 1A:
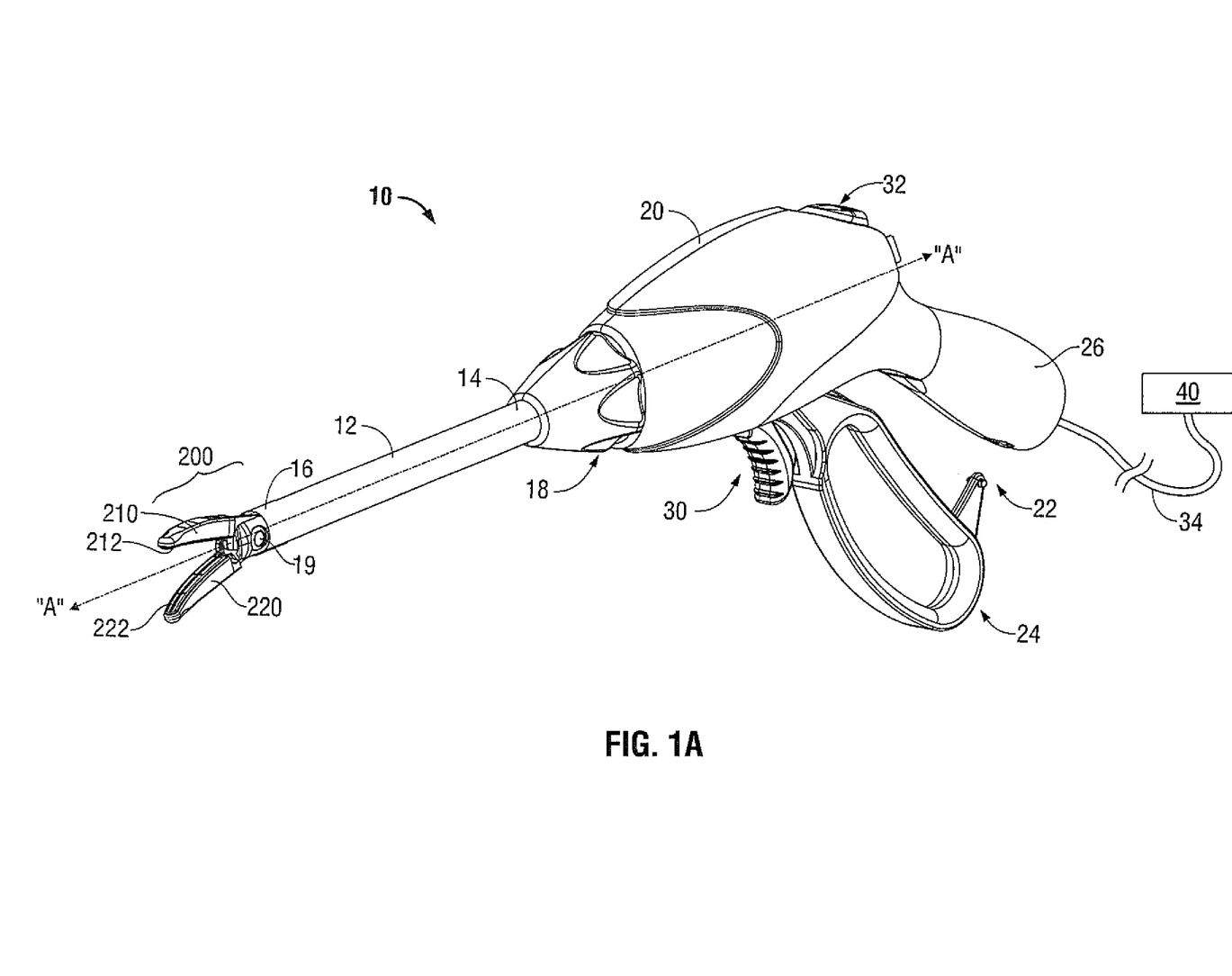
FIG. 1A is a perspective view of an endoscopic forceps having an electrode assembly in accordance with an embodiment of the present disclosure.
Figure 1B:
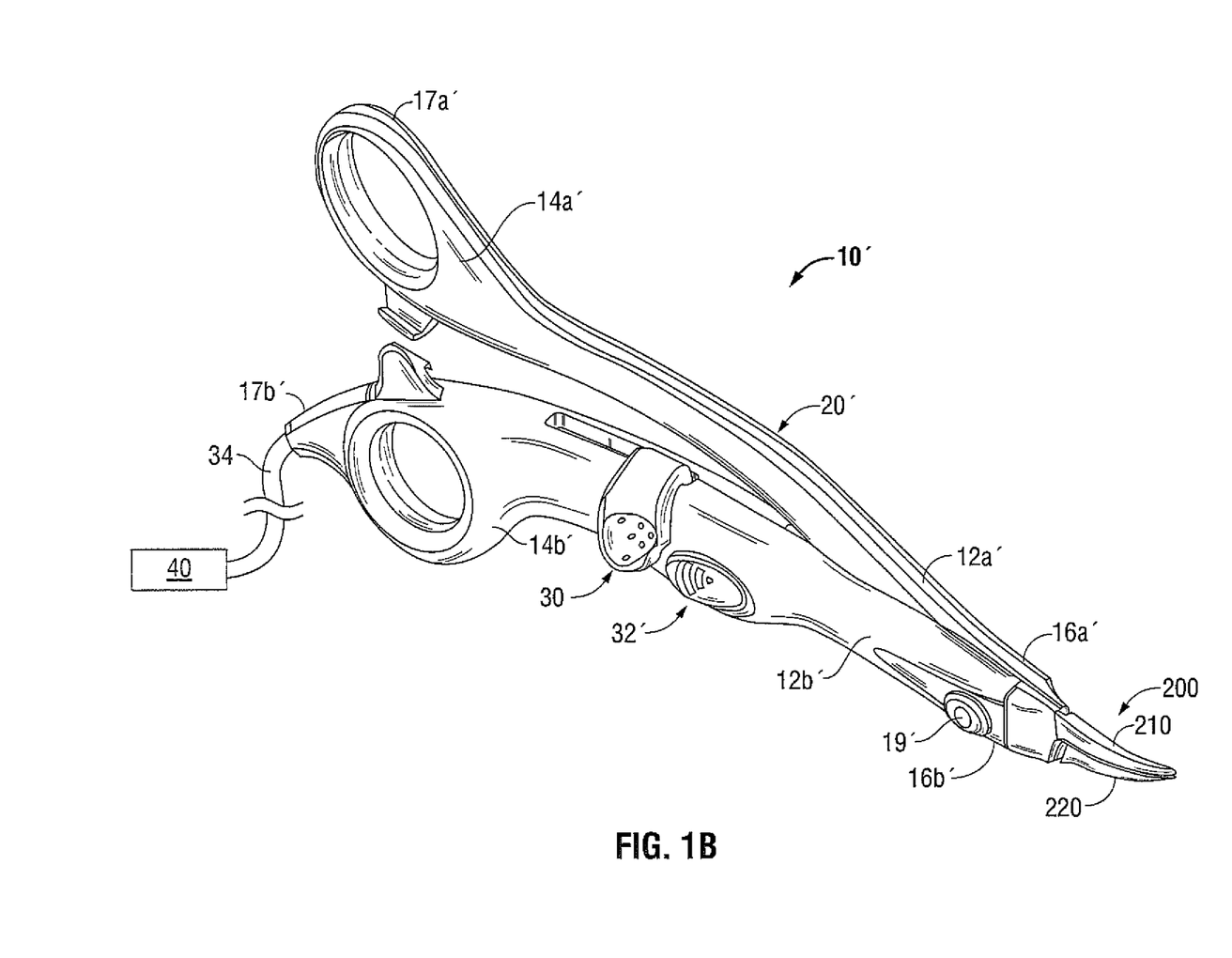
FIG. 1B is a perspective view of an open forceps having an electrode assembly in accordance with an embodiment according to the present disclosure.

Referring now to the figures, FIG. 1A depicts an endoscopic forceps 10 as used in correlation with endoscopic surgical procedures and FIG. 1B depicts an open forceps 10' as used in correlation with open surgical procedures. For the purposes herein, either an endoscopic instrument or an open surgery instrument may be utilized with the novel electrode assembly described herein. It should be noted that different electrical and mechanical connections and other considerations may apply to each particular type of instrument. However, the novel aspects with respect to the electrode assembly described herein and the operating characteristics thereof remain generally consistent with respect to both the endoscopic or open surgery designs.

The forceps 10 is coupled to an electrosurgical energy source and adapted to seal tissue using radiofrequency (RF) energy. The electrosurgical energy source (e.g., generator 40) is configured to output various types of energy such as RF energy having a frequency from about 200 KHz to about 5000 KHz. Forceps 10 is coupled to generator 40 via a cable 34 that is adapted to transmit the appropriate energy and control signals therebetween.

Forceps 10 is configured to support an electrode assembly 200. Forceps 10 typically includes various conventional features (e.g., a housing 20, a handle assembly 22, a rotating assembly 18, and a trigger assembly 30) that enable a pair of jaw members 210 and 220 to mutually cooperate to grasp or clamp, seal and divide tissue. Handle assembly 22 includes a moveable handle 24 and a fixed handle 26 that is integral with housing 20. Handle 24 is moveable relative to fixed handle 26 to actuate the jaw members 210 and 220 via a drive rod (not shown) to grasp and treat tissue. Forceps 10 also includes a shaft 12 that has a distal portion 16 that mechanically engages electrode assembly 200 and a proximal portion 14 that mechanically engages housing 20 proximate rotating assembly 18 disposed on housing 20. Rotating assembly 18 is mechanically associated with shaft 12 such that rotational movement of rotating assembly 18 imparts similar rotational movement to shaft 12 which, in turn, rotates electrode assembly 200.

Electrode assembly 200 includes jaw members 210 and 220 each having an electrode 212 and 222, respectively, associated therewith and on an inner facing surface thereof. One or both of the jaw members 210 and 220 are pivotable about a pin 19 and are movable from a first position such that jaw members 210 and 220 are spaced relative to another, to a second position such that jaw members 210 and 220 are closed and cooperate to clamp or grasp tissue therebetween. As discussed in more detail below, electrode assembly 200 is adapted for use with an RF energy source.

Electrodes 212 and 222 are connected to generator 40 and configured to communicate electrosurgical energy through tissue held therebetween. Electrodes 212 and 222 cooperate to grasp, coagulate, seal, cut, and/or sense tissue held therebetween upon application of energy from generator 40.

Trigger assembly 30 is configured to actuate a knife (not shown) disposed within forceps 10 to selectively sever tissue that is grasped between jaw members 210 and 220. Switch assembly 32 is configured to allow a user to selectively provide electrosurgical energy to electrode assembly 100. A cable 34 connects the forceps 10 to generator 40 that provides electrosurgical energy (e.g., RF energy) to the jaw members 210 and 220 through various conductive paths and ultimately to electrode assembly 200.

Referring now to FIG. 1B, an open forceps 10' is depicted and includes electrode assembly 200 (similar to forceps 10) that is attached to a handle assembly 20' having a pair of elongated shaft portions 12a' and 12b'. Each elongated shaft portion 12a' and 12b' has a proximal end 14a' and 14b', respectively, and a distal end 16a' and 16b', respectively. Similar to forceps 10, electrode assembly 200 includes jaw members 210 and 220 that attach to distal ends 16a' and 16b' of shafts 12a' and 12b', respectively. Jaw members 210 and 220 are connected about a pivot pin 19' that allows jaw members 210 and 220 to pivot relative to one another from the first to second positions for treating tissue (as described above).

Each shaft 12a' and 12b' includes a handle 17a' and 17b', respectively, disposed at the proximal end 14a' and 14b' thereof. Handles 17a' and 17b' facilitate movement of the shafts 12a' and 12b' relative to one another which, in turn, pivot the jaw members 210 and 220 from an open position such that the jaw members 210 and 220 are disposed in spaced relation relative to one another to a clamped or closed position such that the jaw members 210 and 220 cooperate to grasp tissue therebetween.

Forceps 10' includes a trigger assembly 30' (similar to forceps 10) that is configured to actuate a knife (not shown) disposed within shaft 12b'. The knife is configured to allow a user to selectively sever tissue that is grasped between jaw members 210 and 220. One or more of the shafts, e.g., shaft 12a', includes a switch assembly 32' (similar to forceps 10) that is configured to allow a user to selectively provide electrical energy to the electrode assembly 200. In a similar fashion to forceps 10, cable 34' of forceps 10' is internally divided within the shaft 12b' to transmit electrosurgical energy through various conductive pathways to the components of electrode assembly 200.

Figure 2B:
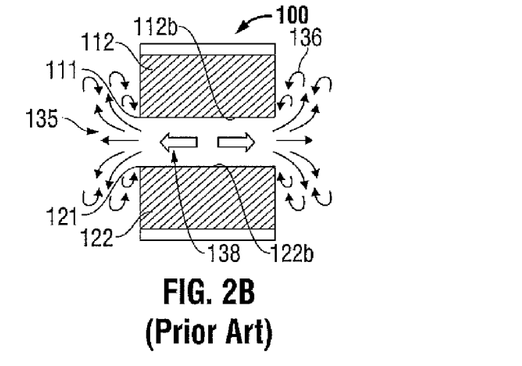
FIG. 2B is a front, cross-sectional view of the prior art electrode assembly of FIG. 2A showing a schematically-illustrated tensor plot of tissue flow during clamping of a tissue.

Referring now to FIGS. 2A and 2B, a traditional prior art electrode assembly is shown having a schematic electric field plot 130 (FIG. 2A) and a tensor field plot 135 of turbulent flow of tissue (FIG. 2B) illustrated thereon. Traditional electrode assembly 100 includes jaw members 110 and 120 each having sealing electrodes 112 and 122 disposed on an inwardlyfacing surface thereof that each have an outer adjoining edge (e.g., edge 111) formed by the intersection of side surface (e.g., side surface 112a) and the respective sealing surface (e.g., sealing surface 112b). Edge 121 is formed in the same fashion at the intersection of side surface 112a and sealing surface 122b. The angle "α" defined by the adjoining surfaces, namely, 112a, 112b and 122a, 122b, respectively, is about 90 degrees.

As shown by the electric field distribution near the edges 111 and 121 of FIG. 2A, this particular end effector 100 configuration tends to produce high current concentration at these edges which can lead to electric field fringing because of the square-shaped configuration of electrodes 110 and 120. Prior art electrodes 110 and 120 may also produce a high concentration of electric field lines 132 and a high concentration of electrical charge at their respective corners 111 and 121 and/or respective surfaces 112a, 122a and 112b, 122b. The combination of high concentration of electric field lines, high concentration of electrical charge of the square-shaped configuration of electrodes 110 and 120 may induce unintended electrical arcing between sealing electrodes 110 and 120 and may lead to undesired tissue effects. As discussed above, tissue burn is calculated using the Arrhenius function (2), where "Ω" is a dimensionless burn parameter (e.g., when Ω=1, a first degree burn is present). An electric field plot 130 of a traditional electrode assembly 130 shows a high degree of energy concentration (e.g., electric field lines 132) at corners 111 and 112 that may produce arcing.

Referring now to FIG. 2B, surface discontinuities may occur anywhere on electrode assembly 100. For example, surface discontinuities may occur at sharp corners (e.g., edges 111 and 121) of the electrodes 112 and 122 and can induce turbulent flow within the tissue being extruded causing high stress tensors 136 that could potentially damage (e.g., shred) tissue cells, as shown in tensor field plot 135. In this configuration, laminar flow within tissue is limited to a region 138 between sealing surfaces 112b and 122b.

Figure 3A:
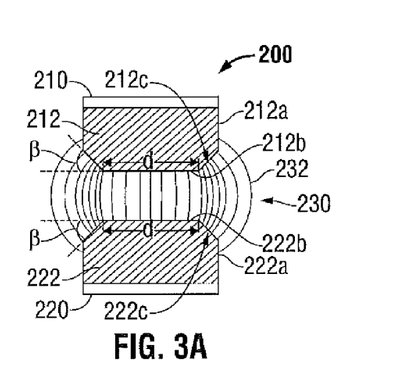
FIG. 3A is a front, cross-sectional view of an electrode assembly in accordance with an embodiment of the present disclosure showing a schematically-illustrated electric field plot.
Figure 4A:
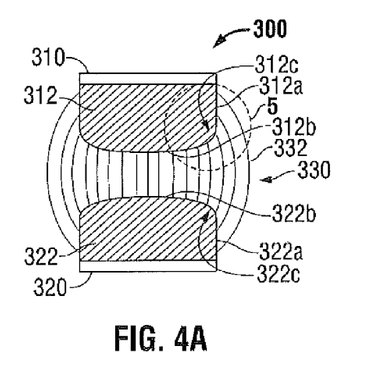
FIG. 4A is a front, cross-sectional view of another electrode assembly in accordance with an embodiment of the present disclosure showing a schematically-illustrated electric field plot.

Turning now to FIG. 3A, an electrode assembly 200 is shown in accordance with an embodiment of the present disclosure (also schematically-illustrating a resulting electric field plot 230). Electrode assembly 200 includes jaw members 210 and 220 each having a chamfered-edge configuration. The chamfered-edge configuration of each jaw member may be utilized for construction of small or large jaw members 210 and 220. Accordingly, jaw members 210 and 220 each include sealing plates or electrodes 212 and 222, respectively, that are chamfered (e.g., angled) at their respective corners 211c and 222c. That is, each jaw member 212, 222 includes a side surface 212a and 222a, respectively, and a sealing surface 212b, 222b, respectively, that meet along a chamfered edge 212c, 222c.

The chamfered configuration 212c, 222c may be configured to have an angle "β" that is relative to the respective side edges 212a and 222a and inner facing sealing surfaces 212b and 222b of jaw members 210 and 220, as shown in FIG. 3A. Angle "β" may be any suitable angle, for example, but not limited from about 5 degrees to about 10 degrees that may be derived empirically. By virtue of chamfering (e.g., rounding or cutting off) the corner of the electrode 212, 222, the width of sealing surfaces 212b and 222b is reduced to a distance "d." In this manner, the surface area of each sealing surface 212b, 222b is reduced to mimic a "small jaw surface area." This method of manufacture facilitates the dispersion of energy (e.g., electric field lines 232), thus mitigating unintended hot spots, tissue shredding and/or arcing at the conjoining edges. As shown in FIG. 3A, the chamfered electrodes 212 and 222 produce an electric field plot 230 (shown by electric field lines 232) that has a lower degree of electric field fringing (when compared to electric field plot 130), a lower concentration of electric field lines 232 at corners that reduces the chance of arcing.

In other embodiments, electrode assembly 200 may be initially manufactured such that sealing surface 212b and 222b, respectively, have a square-cornered configuration similar to a traditional electrode assembly 100. Afterwards, during a manufacturing process the corners may be cut or molded to have the chamfered or rounded configuration 212c and 222c, as described above. During use, sealing surfaces 212b and 222b are configured to be conductive and selectively activated to provide for the primary sealing surface for when tissue is grasped therebetween.

Figure 3B:
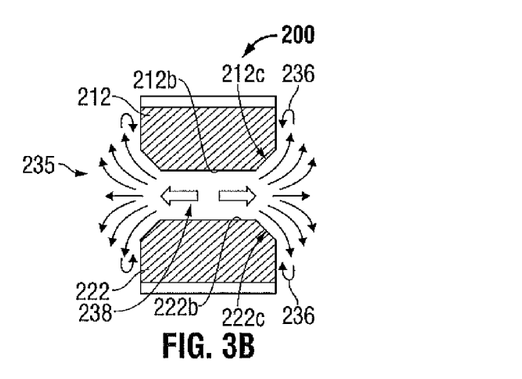
FIG. 3B is a front, cross-sectional view of the electrode assembly of FIG. 3A showing a schematically-illustrated tensor plot of tissue flow during clamping of a tissue.

Referring now to FIG. 3B, similar to electrode assembly 100, surface discontinuities may also occur anywhere on electrode assembly 200. For example, surface discontinuities may occur at the chamfered corners (e.g., edges 212c and 222c) of the electrodes 212 and 222, which can induce turbulent flow within the tissue being extruded causing high stress tensors 236 that could potentially damage (e.g., shred) tissue cells, as shown in tensor field plot 235. In this configuration, laminar flow within tissue is limited to a region 238 between sealing surfaces 212b and 222b.

Referring to FIG. 4A, in accordance with an embodiment of the present disclosure a larger electrode assembly 300 is shown. Jaw assembly 300 includes jaw members 310 and 320 each having a pair of electrodes 312 and 322, respectively. Easements 312c and 322c (e.g., linear transition zones) on electrodes 312 and 322 are included to gradually transition the side surfaces 312a, 322a to the tissue contacting surfaces 312b, 322b (e.g., transitioning from a straight line to a curve).

One advantage in utilizing easement 312c on an electrode assembly (e.g., electrode assembly 300) is having an overall increase in creepage and clearance distances for arcs to travel. That is, the electrode assembly 300 can tolerate or accommodate larger voltage potentials across the electrodes 310 and 320 before any possible arcing may occur during tissue treatment.

Another advantage of utilizing an easement or linear transition zone 312c on electrode assembly 300 is the reduction of tissue shredding and other types of tissue damage that may occur where surface discontinuities take place on the electrodes during clamping and electrosurgical treatment. Typically, vascular tissue is a visco-elastic substance that is forced to continuously flow therewithin when placed under a clamping pressure. Surface discontinuities may occur anywhere on the electrode, typically at sharp corners, which can induce turbulent flow within the tissue being extruded causing high stress tensors that could potentially damage (e.g., shred) tissue cells, if the pressure between the electrodes reaches a threshold. Thus, by substantially eliminating corners or sharp edges on electrodes via easements, high stress tensors at discontinuities will be reduced thereby substantially reducing possible introduction of bubbles, gaps or non-homogeneous regions within the tissue. By preventing tissue shredding, electric arcing may be reduced, since shredded tissue may be a potential arc point(s).

During a surgical treatment, electrodes may encounter bubble formation and release during heating that can also potentially damage tissue at the corners and/or edges, if chamfering is not done properly for many of the same reasons as the above fluid flow problem. The sharper the corner of the more acute, and short, chamfers the more possibility for accumulation of explosive bubbles at any discontinuities (e.g., eddy pockets). Explosive bubbles can also char or damage surrounding cells again creating potential hot spots and arcing at portions of the electrodes. During surgical treatment, once a high current density path 332 forms within the tissue treating zone, an arc may easily break through any such open spot by either wet or dry tracking and potentially damage surrounding tissue.

The novelty of shaping and dimensioning electrodes 312 and 322 to have easements 312c and 322c reduces the non-linearaties in the electric field density and the flow of tissue during clamping. That is, the transition in electric field density and the flow velocities between electrodes 312 and 322 travel through a linear transition zone from sealing surface 312b, 322b to side surface 312a, 322a via easements 312c, 322c. There are various methods of manufacturing easements on electrodes. Some of these methods include using various formulas to accurately and precisely configure the easement on an electrode. Various techniques and/or equations may be utilized in conjunction with an electrode manufacturing process to produce one or more easements on an electrode, such as, a hyperbolic equation, a parabolic equation, exponential equation, a clothoid equation, Bernoulli's equation, an Archimedean equation or any other suitable equation.

Figure 4B:
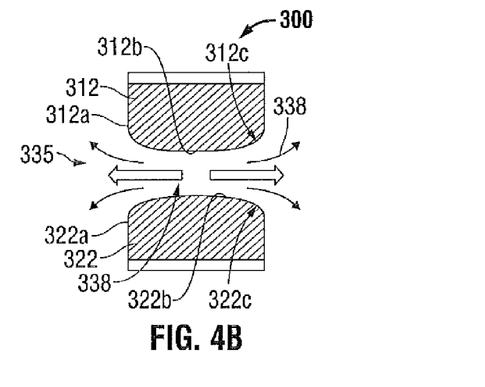
FIG. 4B is a front, cross-sectional view of the electrode assembly of FIG. 4A showing a schematically-illustrated tensor plot of tissue flow during clamping of a tissue.

Referring now to FIG. 4B, as described above, electrode assembly 300 includes linear transition zones or easements 312c and 322c that provide a gradual transition between tissue contacting surfaces 312b and 322b and side surfaces 312a and 312a. In this configuration, easements 312c and 322c also substantially avoid the surface discontinuities described above with regard to electrode assemblies 100 and 200. In this manner, easements 312c and 322c induce laminar flow in most regions of the electrode assembly 300, as shown by laminar flow tensor 338 between tissue contacting surfaces 312b and 322b. Easements 312c and 322c also reduce turbulent flow within tissue around most edges (e.g., easements 312c and 322c) of electrode assembly 300. That is, tensors 338 are shown in a linear configuration in tensor field plot 335, rather than turbulent high stress tensors (e.g., high stress tensors 136).

Figure 5:
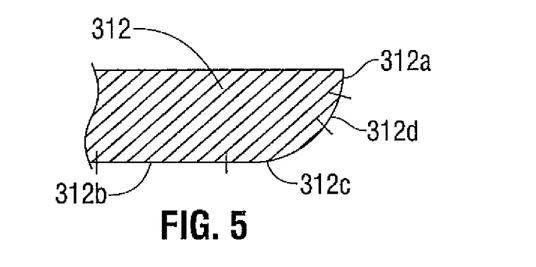
FIG. 5 is an enlarged view of the area of detail of the electrode of FIG. 4A.

FIG. 5 illustrates an enlarged view of electrode 312 of the electrode assembly 300 having one or more easements or linear transition zones 312c and 312d. Electrode 312 includes a side surface 312a, a tissue energizing electrode surface 312b, and a conjoining edge. The conjoining edge is formed by a first predetermined angle to define a first linear transition zone or easement 312c and by a second predetermined angle to define a second linear transition zone or easement 312d.

Figure 6:
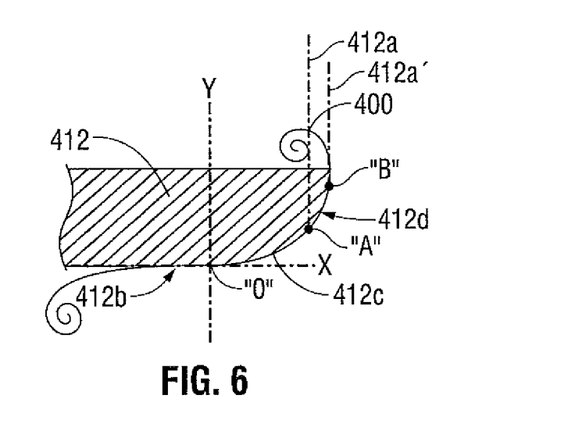
FIG. 6 is a front, cross-sectional view of an electrode in accordance with an embodiment of the present disclosure schematically-illustrating a graphical plot superimposed thereon.

FIG. 6 illustrates a portion of an electrode assembly in accordance with an embodiment of the present disclosure having a graphical plot superimposed thereon. One embodiment disclose herein describes a method of manufacturing an easement on an electrode and includes providing a clothoid spiral equation (e.g., a Euler Spiral) to determine the position of the easement on the individual electrode. An example of a clothoid spiral equation includes the following Fresnel integrals:

$$x = + \int_0^A \cos\left(\frac{\pi}{2}s^2\right) ds \quad (3)$$

$$y = - \int_0^A \sin\left(\frac{\pi}{2}s^2\right) ds \quad (4)$$

where s is the arc length of the line 400.

In this embodiment, electrode 412 includes a vertical tangent or side surface 412a and a tissue engaging sealing surface 412b, a first easement or linear transition zone 412c and a second easement or linear transition zone 412d. By utilizing the clothoid spiral, an easement may be configured and dimensioned to include a tissue contacting surface including a sealing surface 412b having a straight-line configuration (e.g., along the x-axis) and terminating at the origin "0." From the origin "0," easement 412c is formed along the electrode 412 and continues to point "A" along line 400 of electrode 412. At this point, a vertical tangent may be formed on side surface 412a and continue in a vertical direction to any suitable length (e.g., along the y-axis), Alternatively, electrode 412 may further include easement 412d that may be formed alongside the electrode, for example, from point "A" to point "B." In this configuration, another vertical tangent or side surface 412a' may be formed and continue in a vertical direction to any suitable length from point "B." Easement 412d may have a radius equal to the curvature of coordinates (e.g., x, y) between points "A" and "B" or any other suitable radius. In any of these embodiments, electrode 412 includes the benefits of having easement(s) 412c, 412d, as discussed above with other embodiments.

Figure 7:
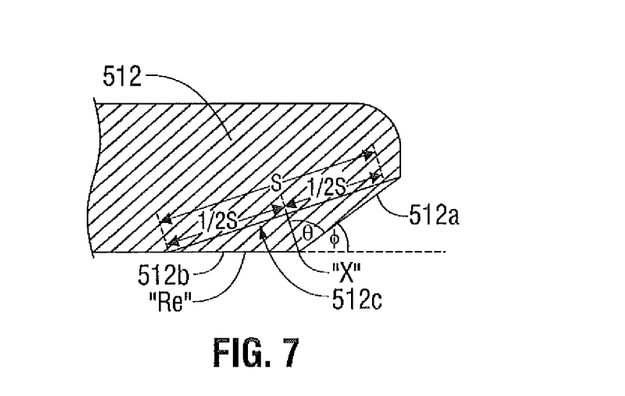
FIG. 7 is a front, cross-sectional view of an electrode in accordance with another embodiment of the present disclosure schematically-illustrating a graphical plot superimposed thereon.

FIG. 7 depicts a portion of an electrode 510, in accordance with another embodiment of the present disclosure having a graphical plot superimposed thereon.

In this method of manufacturing, an easement is created on electrode 512 by calculating a parabolic equation utilizing angles "Θ" and "φ" shown on FIG. 7. Angle "φ" is the angle of a tangent taken along the tissue energizing sealing surface 512b relative to the angled edge 512d. Angle "Θ" is calculated using equation (3) below. The parabolic equation determines the position of the easement on electrode 512. An example of a parabolic equation includes the following derivations:

$$\Theta = \frac{180 - \phi}{2} \quad (3)$$

$$R_m = \frac{s^2}{B} = \left[\frac{C * \sin^2(\Theta)}{\cos(\Theta)}\right] \quad (4)$$

$$C \cong R_m * \left[\frac{\cos(\Theta)}{\sin^2(\Theta)}\right] \quad (5)$$

where "C" is the length of vertical side surface 512a before electrode 512 is modified (e.g., cut or chamfered), "$R_m$" is the minimum radius, "S" is the length of the easement, "B" is distance from a midpoint of the easement 512c to a corner of a pre-cut portion of electrode 512 that is formed by sealing surface 512b' and angled portion 512d. In this embodiment, an easement radius "$R_e$" may be calculated at any point along the easement. The equation below may be used to calculate radius "$R_e$":

$$R_e \cong R_m * \left[1 + \frac{4 * x^2}{R_m^2}\right] \quad (6)$$

where "$R_e$" is the easement radius, "$R_m$" is the minimum radius and "x" is a predetermined point.

By utilizing the parabolic equation, an easement may be configured and dimensioned to be formed having a length "S" by choosing desired valued for "B," "C," and/or "$R_m$." These values, as previously described, may be found by appropriate empirical testing and/or finite element analysis.

The above-described calculations may be associated with a manufacturing process of electrode assemblies 212, 312, 412 and 512. For example, computer-aided manufacturing machines that are instructed by a software may be programmed to receive instructions on the desired easement specifications. The software may include any one of the above-described calculations for creating an easement on an electrode. In other examples, any of the above-described calculations may be manually interpreted by an operator and, subsequently, the electrode may be modified by any suitable machining process to include easements as described above.

Electrodes may be attached to their respective jaw members by stamping, by overmolding, by casting, by overmolding a casting, by coating a casting, by overmolding a stamped electrically conductive sealing plate and/or by overmolding a metal injection molded seal plate or in other ways customary in the art. All of these manufacturing techniques may be employed to produce the above-described jaw members and include an electrically conductive electrode with an easement configuration for contacting and treating tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrode assembly for use with an electrosurgical instrument, the electrode assembly comprising:
   opposing jaw members;
   each one of the opposing jaw members including an electrode including a tissue contacting surface, a side surface, and a conjoining edge associated with the tissue contacting surface and the side surface, the conjoining edge chamfered at a predetermined angle relative to the tissue contacting surface and the side surface to define a linear transition zone, the predetermined angle determinative of a position of the linear transition zone on each electrode to reduce arcing and induce laminar tissue flow between the opposing jaw members during activation of the electrosurgical instrument.

2. An electrode assembly according to claim 1, wherein the conjoining edge is calculated from at least one equation selected from the group consisting of a hyperbolic equation, a parabolic equation, exponential equation, a clothoid equation, Bernoulli's equation, and an Archimedean equation.

3. An electrode assembly according to claim 1, wherein the tissue contacting surface is configured to treat tissue.

4. An electrode assembly according to claim 1, wherein the side surface is configured to treat tissue.

5. An electrode assembly according to claim 1, wherein the side surface is configured to be electrically insulated.

6. An electrode assembly according to claim 1, wherein the electrode is adapted to connect to an electrosurgical energy source to electrosurgically treat tissue.

7. An electrode assembly according to claim 1, wherein the predetermined angle is about 5 degrees to about 10 degrees.

8. A method for manufacturing an electrode assembly for use with an electrosurgical instrument, the method comprising the steps of:
   providing an electrode assembly including:
     a pair of opposing jaw members;
     each one of the opposing jaw members including an electrode, at least one electrode including a tissue contacting surface and a side surface; and
   determining a position of a conjoining edge to reduce arcing and induce laminar tissue flow between the opposing jaw members during activation of the electrosurgical instrument by determining a first angle relative to the tissue contacting surface and the side surface to define a first linear transition zone and by determining a second angle relative to the tissue contacting surface and the side surface to define a second linear transition zone; and
   forming the conjoining edge at the position to thereby reduce arcing and induce laminar tissue flow between the opposing jaw members during activation of the electrosurgical instrument.

9. A method according to claim 8, wherein the step of determining the first predetermined angle includes solving at least one equation selected from the group consisting of a hyperbolic equation, a parabolic equation, exponential equation, a clothoid equation, Bernoulli's equation, and an Archimedean equation.

10. A method according to claim 8, wherein the step of forming is selected from the group consisting of cutting and molding.

11. A method according to claim 8, wherein the first predetermined angle is about 5 degrees to about 10 degrees.

12. A method for manufacturing an electrode assembly for use with opposing jaw members of an electrosurgical instrument, the method comprising the steps of:
   providing opposing jaw members and an electrode including a side surface having a vertical configuration relative to the jaw member and a tissue contacting sealing surface having a horizontal configuration relative to the jaw member; and
   determining a position of a conjoining edge to reduce arcing between the opposing law members during activation of the electrosurgical instrument by determining an angle relative to the tissue contacting surface and the side surface to define a linear transition zone;
   chamfering the edges of the electrode at the angle, the chamfered edges configured to reduce a width of the tissue contacting sealing surface and create the linear transition zone to reduce arcing between the opposing jaw members.

13. A method according to claim 12, wherein the step of chamfering is selected from the group consisting of cutting and molding.

14. A method according to claim 12, wherein the angle is about 5 degrees to about 10 degrees.

* * * * *